United States Patent [19]

Forssmann

[11] Patent Number: 4,782,044
[45] Date of Patent: Nov. 1, 1988

[54] COMPOSITION CONTAINING CORDIODILATIN OR FRAGMENTS THEREOF AND METHODS OF OBTAINING CARDIODILATIN

[75] Inventor: Wolf-Georg Forssmann, Heidelberg, Fed. Rep. of Germany

[73] Assignee: ORGANON-Medizinisch-Molekularbiologische Forschungsgellschaft m.b.H, Heidelberg, Fed. Rep. of Germany

[21] Appl. No.: 140,736

[22] Filed: Jan. 4, 1988

Related U.S. Application Data

[62] Division of Ser. No. 769,627, Aug. 20, 1985, Pat. No. 4,751,284.

[30] Foreign Application Priority Data

Dec. 24, 1983 [DE] Fed. Rep. of Germany ....... 3346953

[51] Int. Cl.[4] ............................................. A61K 37/02
[52] U.S. Cl. ........................................ 514/12; 514/14; 514/15; 514/16; 514/17; 530/324; 530/327; 530/328; 530/329
[58] Field of Search ....................... 514/12, 14, 15, 16, 514/17; 530/324, 327, 328, 329

[56] References Cited

U.S. PATENT DOCUMENTS 4,604,234 8/1986 Fujii et al. ............................ 530/350
4,638,050 1/1987 Aoki et al. ........................... 530/350
4,675,382 6/1987 Murphey ............................. 530/350

FOREIGN PATENT DOCUMENTS 0159943 10/1985 European Pat. Off. .

OTHER PUBLICATIONS

Lazure et al., *FEBS Letters*, vol. 172, No. 1, pp. 80–86, "Atrial Pronatriodilatin: A Precursor for Natriuretic Factor and Cardiodilatin".
Nakayama et al, *Nature*, vol. 310, No. 3979, pp. 699–701, "m-RNA Sequence for Human Cardiodilatin-Atrial Natriuretic Factor Precursor and Regulation of Precursor m-RNA in Rat Atria".
Forssman et al, "The Right Auricle of the Heart is an Endocrine Organ", *Anatomy and Embryology*, vol. 168, 307-313, 1983.

*Primary Examiner*—John Kight
*Assistant Examiner*—Nathan M. Nutter
*Attorney, Agent, or Firm*—Felfe & Lynch

[57] ABSTRACT

This invention teaches therapeutic compositions containing the hormone cardiodilatin of active fragments thereof, as well as methods for obtaining the cardiodilatin. The compositions are useful in relaxing smooth, blood vessel muscles.

15 Claims, 10 Drawing Sheets

CARDIODILATIN - Fragment
(1-7) Variant Met (Pos.3),
Asn (Pos.5), Ala (Pos.6)
Retention time : 35,5 Min.
Gradient :  A (0,1% TFA in H2O),
            B (0,1% TFA in Methanol)
Min. 0-5 (100%A), Min. 5-35
(0-40%B)

IPMYNAY

```
FLOW RATE : 1,0
FLOW MODE : QG
PRESSURE  : 0042
COLUMN    : HD-SIL-18-5S-100 H
CHAN 1 : 200
CHAN 2 :
MOBILE PHASE H2O-MEOH (0,1% TFA)          JUL-30-84  10:29
MOBILE PHASE FILE 3
TIME   %A    %B        CHANNEL  1   RUN 47   FILE  1   METHOD
 0.0  100.0  0.0       INDEX 22
 5.0  100.0  0.0
35.0   60.0 40.0       PEAK      AREA%    RT      AREA
40.0  100.0  0.0         1        5.82    283     1549
                         2       12.81    316    34069
END OF PROGRAMMED RUN    3       86.61    355   230393

TOTALS    99.99          266011
```

CARDIODILATIN – Fragment
(23 – 28)
Retention time : 28,8 Min.
Gradient : A (0,1% TFA in $H_2O$)
B (0,1% TFA in Methanol)
Min. 0-5 (100%A), Min. 5-35 (0-50% B)

```
END OF RUN    10:40:06
END OF PROGRAMMED RUN

IDKMPL
   NO : 1
RUN ON JUL-18-84   10:00
FLOW RATE    : 1,0
FLOW MODE    : QG
TEMPERATURE  : 35
PRESSURE     : 0046
COLUMN       : HD-SIL-18-5S-100N

CHAN 1 : 220
MOBILE PHASE : H2O METHANOL
MOBILE PHASE FILE 4

TIME    %A     %B
 0.0   100.0   0.0
 5.0   100.0   0.0
35.0    60.0  40.0
40.0   100.0   0.0
```

CARDIODILATIN - Fragment
(38-44)
Retention time : 25,9 Min.
Gradient: A (0,1% TFA in H2O)
B (0,1% TFA in Methanol)
Min. 0-5 (100%A), Min. 5-35(0-50% B)

INJECT 15:51:38 1

224
233
245
278 259
285
312

END OF RUN 16:31:41

LSEQDEE
NO:1
RUN ON SEP-20-84    15:51

FLOW RATE    : 1.0
FLOW MODE    : OG
TEMPERATURE: 40
PRESSURE     : 0070
COLUMN       : HD-SIL-18-5S-100

CHAN1: 220
MOBILE PHASE FILE 4

SEP-20-84    15:51

CHANNE 1    RUN 61    FILE 1    METHOD 0
INDEX 23

| TIME | %A | %B |
|------|------|------|
| 0.0 | 100.0 | 0.0 |
| 5.0 | 100.0 | 0.0 |
| 35.0 | 50.0 | 50.0 |
| 40.0 | 100.0 | 0.0 |

| PEAK | AREA% | RT | AREA |
|------|-------|-----|------|
| 1 | 3,094 | 224 | 3168 |
| 2 | 6,329 | 233 | 6482 |
| 3 | 1,799 | 245 | 1843 |
| 4 | 87,02 | 259 | 89123 |
| 5 | 1,758 | 285 | 1800 |
| TOTALS | 99,98 | | 102416 |

CARDIODILATIN-Fragment
(78-84)
Retention time: 24,5 Min.
Gradient: A (0,1% TFA in H2O)
B (0,1% TFA in Methanol)
Min. 0-5 (100%A), Min. 5-50 (0-50% B)

INJECT   13:21:37   1

END OF RUN   14:11:39

IPSORSA
NO:1
RUN ON DEC-28-84   13:21

FLOW RATE : 1.0
FLOW MODE: OG
PRESSURE  : 0082
COLUMN    : HD-SIL-18-5S-100 N
CHAN 1    : 230
MOBILE PHASE FILE 4
TIME    %A    %B 0.0   100.0   0.0
5.0   100.0   0.0
40.0   50.0   50.0

END OF PROGRAMMED RUN

| PEAK | AREA% | RT | AREA |
|---|---|---|---|
| 1 | 8,606 | 202 | 19405 |
| 2 | 1,644 | 224 | 3707 |
| 3 | 16,37 | 234 | 36910 |
| 4 | 46,91 | 245 | 105771 |
| 5 | 12,32 | 253 | 27781 |
| 6 | 1,585 | 394 | 3575 |
| 7 | 12,57 | 489 | 28342 |
| TOTALS | 99,99 | | 225491 |

INJECT 14:45:30 1

246
270

END OF RUN 15:35:32

PRSLRRSS
NO: 1
RUN ON DEC-15-84  14:45
FLOW RATE : 1,0
FLOW MODE : QG
PRESSURE  : 0116
COLUMN    : HD-SIL-18-5S-100N
CHAN 1    : 230
MOBILE PHASE FILE 4
TIME  %A    %B
 0.0  100.0  0.0
 5.0  100.0  0.0
40.0   50.0 50.0

END OF PROGRAMMED RUN

CARDIODILATIN-Fragment
(96-104)
Retention time: 27,8 Min.
  radient : A (0,1% TFA in H2O),
            B (0,1% TFA in Methanol)
  Min. 0-5 (100%A), Min. 5-50 (0-50%B)

| PEAK | AREA% | RT | AREA |
|---|---|---|---|
| 1 | 100 | 270 | 57862 |
| TOTALS | 100 | | 57862 |

CARDIODILATIN-Fragment
(108-114) Variant Tyr (Pos. 107)
cyclic form
Retention time: 34,9 Min.
Gradient: A (0,1% TFA in H$_2$O)
B (0,1% TFA in Methanol)
Min. 0-5 (100%A), Min. 5-35 (0-50%B)

```
INJECT    09:36:21 1

END OF RUN    10:16:23
CYCLO-YGRMDRIG
NO : 1
RUN ON SEP-25-84   09:36

FLOW RATE  : 1.0
FLOW MODE  : QG
TEMPERATURE: 40
PRESSURE   : 0070
COLUMN     : HD-SIL-18-10-100

CHAN 1 : 230
MOBILE PHASE FILE 4
TIME   %A    %B 0.0   100.0   0.0
5.0   100.0   0.0
35.0   50.0  50.0
40.0  100.0   0.0
```

| PEAK | AREA % | RT | AREA |
|------|--------|-----|--------|
| 1 | 1.123 | 205 | 1557 |
| 2 | 6.114 | 265 | 8475 |
| 3 | 92.76 | 349 | 128581 |
| TOTALS | 99.99 | | 138613 |

COMPOSITION CONTAINING CORDIODILATIN OR FRAGMENTS THEREOF AND METHODS OF OBTAINING CARDIODILATIN

This application is a divisional of U.S. application Ser. No. 769,627, filed Aug. 20, 1985, now U.S. Pat. No. 4,751,284.

The invention concerns a new peptide hormone and a process for its preparation.

From electron microscopic investigations, it was known that the right heart auricle (atrium) of the pig contains two different cell types, one of which has the morphology of endocrine cells (secretary granular). By means of morphological and histological investigations of the right atrium, however, no hormone substance, such as that of the type already known in myoendocrine cells of the heart auricle, could be determined. On the other hand, many of the known neuropeptide hormones were ascertained in the heart nerves.

It has now been found that atrium extracts (heart auricle), besides an already described diuretic activity (cf. J.-P. Marie, H. Guillemont, P. Y. Hatt, Pathol. Biol., 24 (1976) 549–554), surprisingly display effects on the ionotropia of the heart muscle itself or influences on the smooth blood vessel musculature, as well as influences on the secretion of perspiration. Furthermore, it was found that these biological actions were caused by a new peptide hormone which, having regard to its actions, has a great clinical and therapeutic importance, especially with regard to the diagnosis and therapy of hypertonia.

Therefore, the subject of the invention is the new peptide hormone cardiodilatin with the N-terminal amino acid sequence:

Asn-Pro-Val-Tyr-Gly-Ser-Val-Ser-Asn-Ala-Asp-
Leu-Met-Asp-Phe-Lys-Asn-Leu-Leu-Asp-His-
Leu-Glu-Asp-Lys-Met-Pro-Leu-Glu-Asp-Glu-
Ala-Met-Pro-Pro-Gln-Val-Leu-Ser-Glu-Gln-Asp-
Glu-Glu-Val-Gly-Ala-Pro-Leu-Pro-Leu-Leu-Glu-
Glu-Val-Pro-Pro-Trp-Thr-Gly-Glu-Val-Asn-Pro of the composition:

Asp/Asn 14, Thr 3, Ser 15, Glu/Gln 12, Pro10, Gly 12, Ala 10, Val 7, Met 4, Ile 1, Leu 15, Tyr 2, Phe 3, Lys 4, His 2, Arg 10, Trp 2, a length of 126 amino acid residues and an isoelectric point I.P. of 6 to 6.5.

Furthermore, it has been found that fragments, especially C-terminal fragments and the fragments of the peptide hormone cardiodilatin present between two Met residues of the peptide chain display the biological activities of cardiodilatin, even though, in part, in weakened form.

Therefore, the subject of the invention are also the fragments of the peptide hormone cardiodilatin present between two Met residues of the peptide chain, such as e.g. the fragment with the amino acid sequence Asp-Phe-Lys-Asn-Leu-Leu-Asp-His-Leu-Glu-Asp-Lys-Hse (1) or the fragment with the amino acid sequence Pro-Leu-Glu-Asp-Glu-Ala-Hse (2) and the N-terminal fragment Asn-Pro-Val-Tyr-Gly-Ser-Val-Ser-Asn-Ala-Asp-Leu-Hse, as well as in each case the C-terminal remaining rump sequence of the cardiodilatin 126 shortened by the stated homoserine peptides. One obtains these framents by partial cyanogen bromide fissions, whereby the N-terminal shortening of the cardiodilatin leads to separated off fragments which, in each case, end C-terminally with homoserine (Hse). The N-terminal shortened fragments of cardiodilatin formed by fission with arginine-specific endopeptidase also display qualitatively the same biological effectiveness as the parent molecule even though in weakened form.

Furthermore, a series of cardiodilation fragments were prepared either synthetically by Merrifield synthesis or by fission of the cardiodilatin with specifically-splitting proteases and investigated. The Merrifield synthesis was thereby so carried out that, beginning at the C-terminal end, the amino acid chain was, in each case, lengthened by two amino acids, split off, investigated and, according to the same principle, lengthened by a further two amino acids. This process was repeated as often as was necessary for the fragments obtained and more closely defined further below.

The fragments prepared display an interesting biological activity, namely, they are suitable for the formation of antibodies which are able to recognise the whole cardiodilatin and, therefore, can also be used for its detection in the scope of an immune assay. There are suitable not only the numerous known embodimental forms of the RIA (radio-immune assay) but also of the EIA (enzyme immune assay). Furthermore, it was shown that some of the fragments also display the vasodilatory effectiveness of cardiodilatin, especially the fragment containing the amino acids 39 to 126 and the corresponding fragments lengthened N-terminally up to amino acid 7.

Therefore, a further subject of the invention are the following stated fragments, which are characterised by the HPLC data:

Fragments which include the amino acid positions 1 to 7:
Asn-Pro-Val-Tyr-Gly-Ser-Val, as well as its structure variation Met (position 3), Asn (position 5) and Ala (position 6), both also N-terminally lengthened by the sequence Lys-Lys; e.g. Lys-Lys-Asn-Pro-Val-Tyr-Gly-Ser-Val.

Fragment 8 to 19:
Ser-Asn-Ala-Asp-Leu-Met-Asp-Phe-Lys-Asn-Leu-Leu (see FIG. 3)

Fragment 23 to 28:
Glu-Asp-Lys-Met-Pro-Leu, as well as its structure variation Glu (position 24) (see FIG. 4).

Fragment 29 to 37:
Glu-Asp-Glu-Ala-Met-Pro-Pro-Gln-Val, as well as its variants with Val (pos. 32 and 33) and Glu (pos. 37).

Fragment 38 to 44:
Leu-Ser-Glu-Gln-Asp-Glu-Glu, as well as its variants with Pro (position 41), Asn (position 42). (FIG. 5).

Fragment 63 to 70:
Asp-Pro-Ser-Gln-Arg-Asp-Gly-Gly, as well as its variants with Ser (position 63), Ala (position 65) (FIG. 6).

Fragment 73 to 79:
Gly-Arg-Gly-Pro-Trp-Asp-Pro, as well as its variants with Phe (position 77), Ser (position 79).

Fragment 78 to 84:
Asp-Pro-Ser-Asp-Arg-Ser-Ala, as well as its variants with Ser (position 79) (FIG. 7).

Fragment 86 to 92:
Leu-Lys-Ser-Lys-Leu-Arg-Ala.

Fragment 96 to 104:
Gly-Pro-Arg-Ser-Leu-Arg-Arg-Ser-Ser, as well as its variants with Ala (position 96) (FIG. 8).

Fragment 108 to 114:
with an additional Tyr (position 107), Tyr-Gly-Arg-Met-Asp-Arg-Ile, as well as its cyclic form (FIG. 9)

—Tyr—Glu—Arg—Met—Asp—Arg—Ile—Gly—.

Fragment 117 to 126:
Ser-Gly-Leu-Gly-Cys-Asn-Ser-Phe-Arg-Tyr and its dimeric disulphide.

Fragment 120 to 126:
Gly-Cys-Asn-Ser-Phe-Arg-Tyr and its dimeric disulphide

Fragment 39 to 126:
Ser-Glu-Gln-Asn-Glu-Glu-Val-Gly-Ala-Pro-Leu-Pro-Leu-Leu-Glu-Glu-Val-Pro-Pro-Trp-Thr-Gly-Glu-Val-Asp-Pro-Ser-Gln-Arg-Asp-Gly-Gly-Ala-Leu-Gly-Arg-Gly-Pro-Trp-Asp-Pro-Ser-Asp-Arg-Ser-Ala-Leu-Leu-Lys-Ser-Lys-Leu-Arg-Ala-Leu-Leu-Ala-Gly-Pro-Arg-Ser-Leu-Arg-Arg Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr, as well as its structure variants in the region of the positions 39 to 65 Ser-Glu-Pro-Asn-Glu-Glu-Ala-Gly-Ala-Ala-Leu-Ser-Pro-Leu-Pro-Glu-Val-Pro-Pro-Trp-Thr-Gly-Glu-Val-Ser-Pro-Ala.

BRIEF DESCRIPTION OF THE DRAWINGS

FIG. 2a shows a graphic illustration of the HPLC curve of cardiodilatin fragment Lys-Lys- (1–7).

Figure 1:
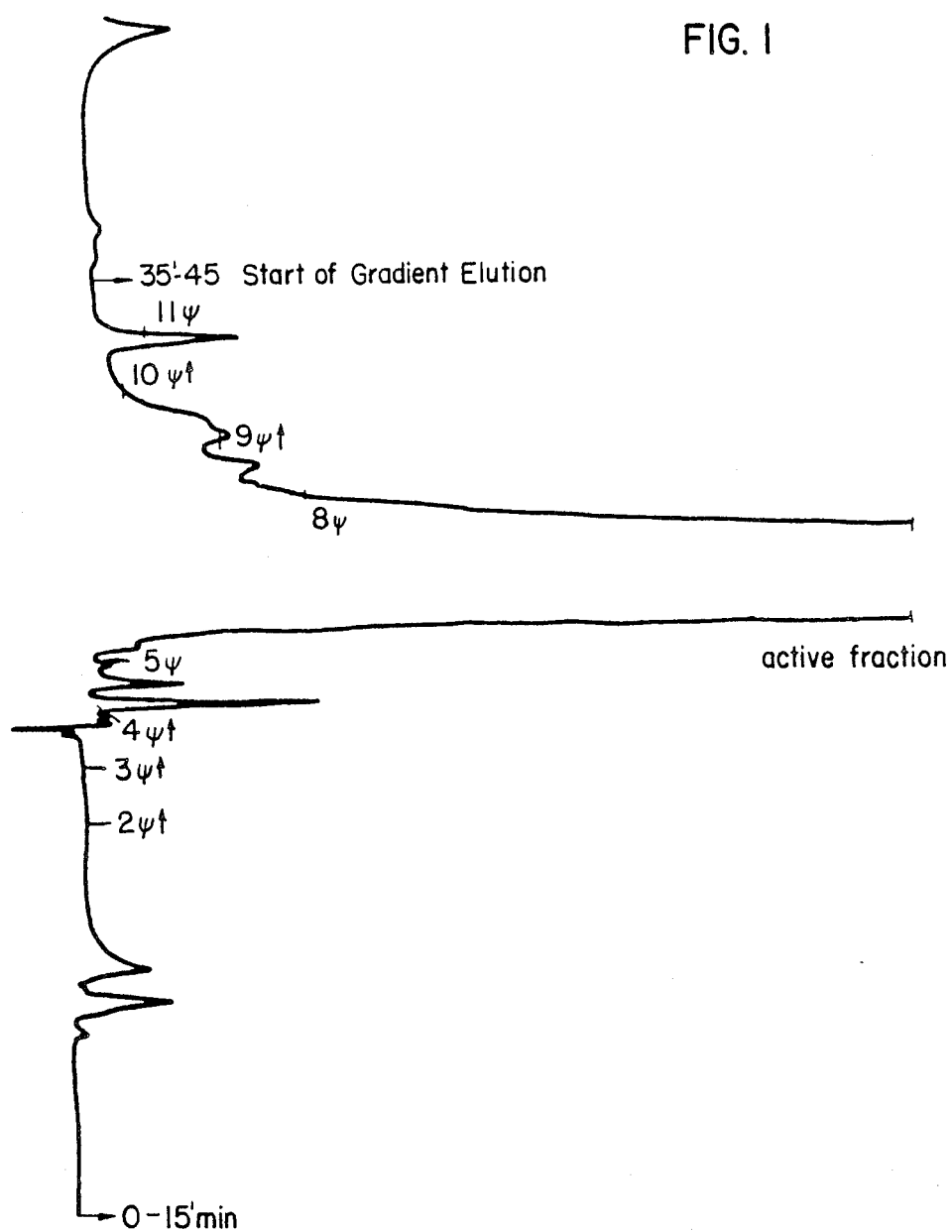
FIG. 1 shows a graphic illustration of the HPLC curve of the eluate of Example 2.
Figure 2:
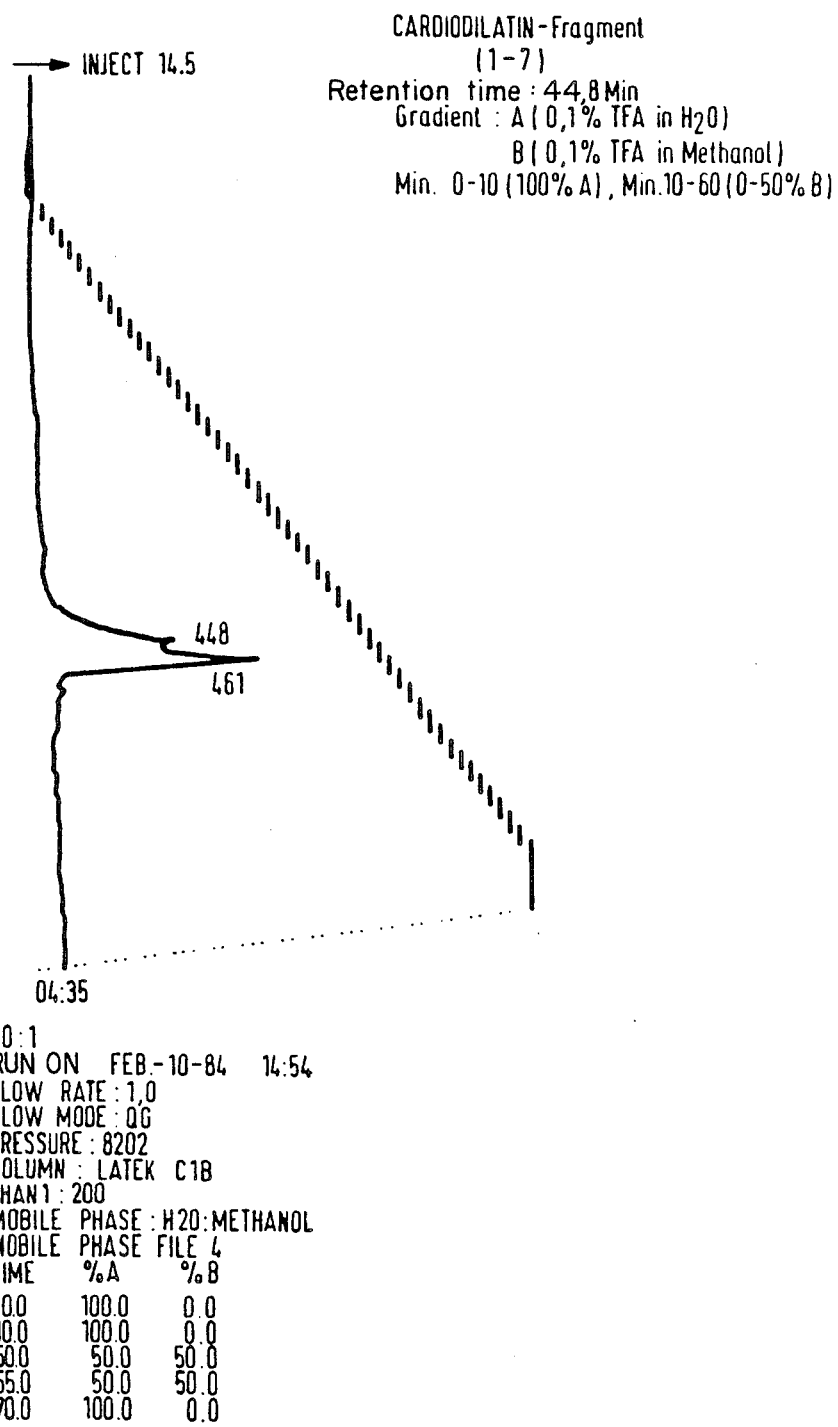
FIG. 2 shows a graphic illustration of the HPLC curve of cardiodilatin fragment (1–7).
Figure 2B:
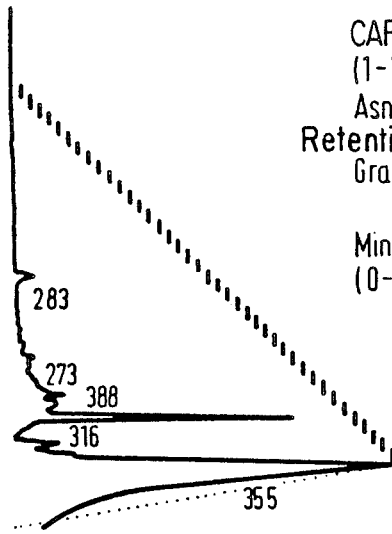
FIG. 2b shows a graphic illustration of the HPLC curve cardiodilatin fragment (1–7), Met (Pos. 3), Asn (Pos. 5) and Ala (Pos. 6).
Figure 3:
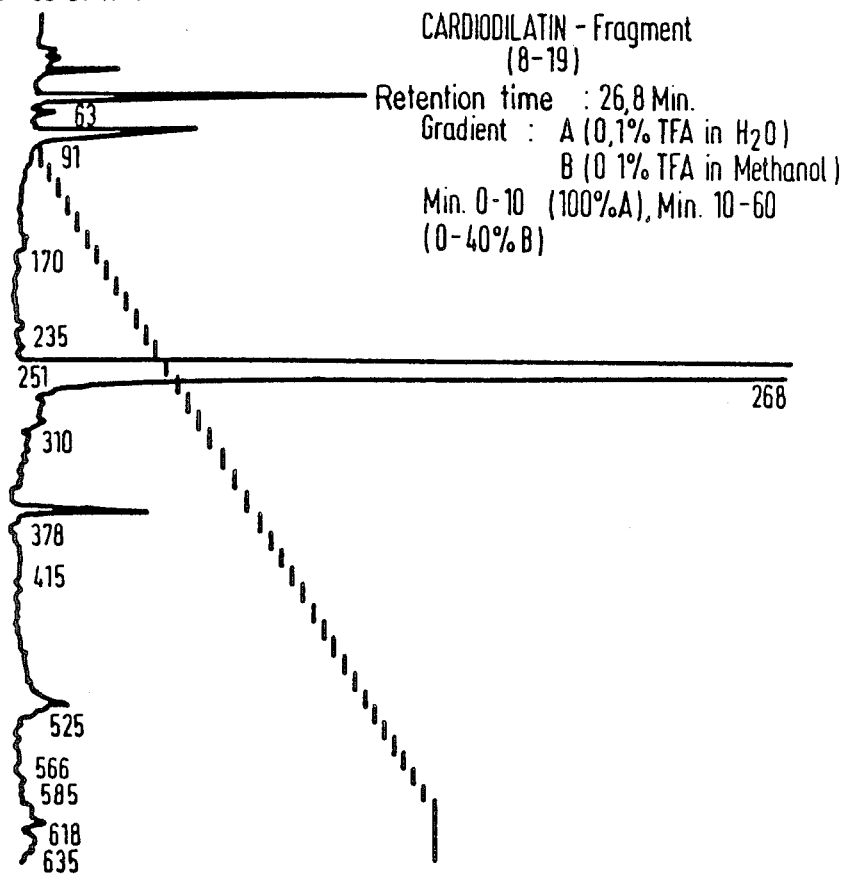
FIG. 3 shows a graphic illustration of the HPLC curve of cardiodilatin fragement (8–19).
Figure 4:
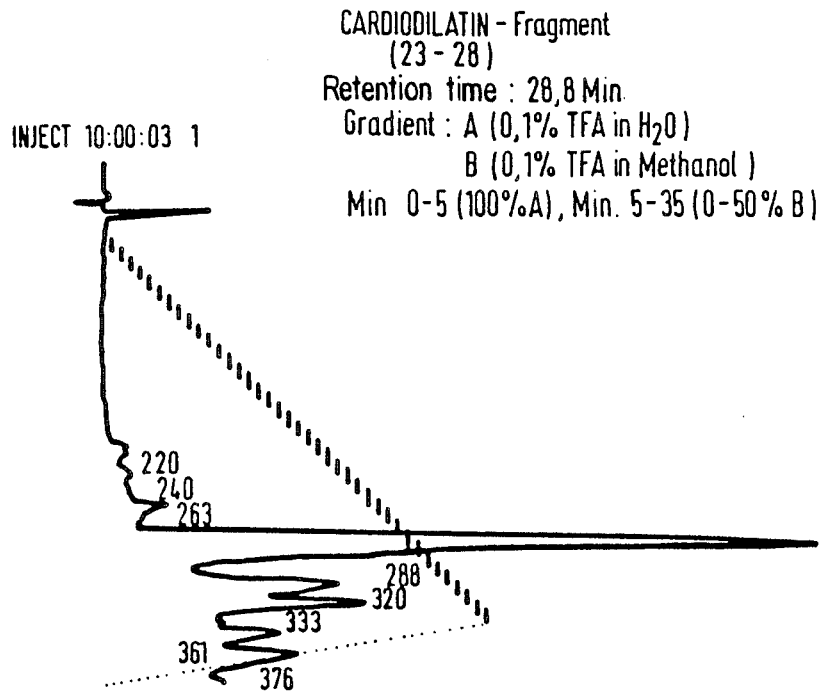
FIG. 4 shows a graphic illustration of the HPLC curve of cardiodilatin fragment (23–28).
Figure 5:
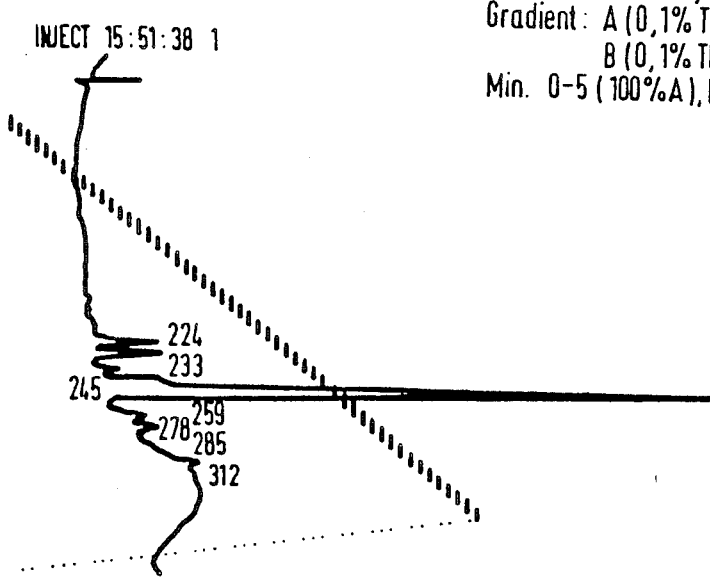
FIG. 5 shows a graphic illustration of the HPLC curve of cardiodilatin fragment (38–44).
Figure 6:
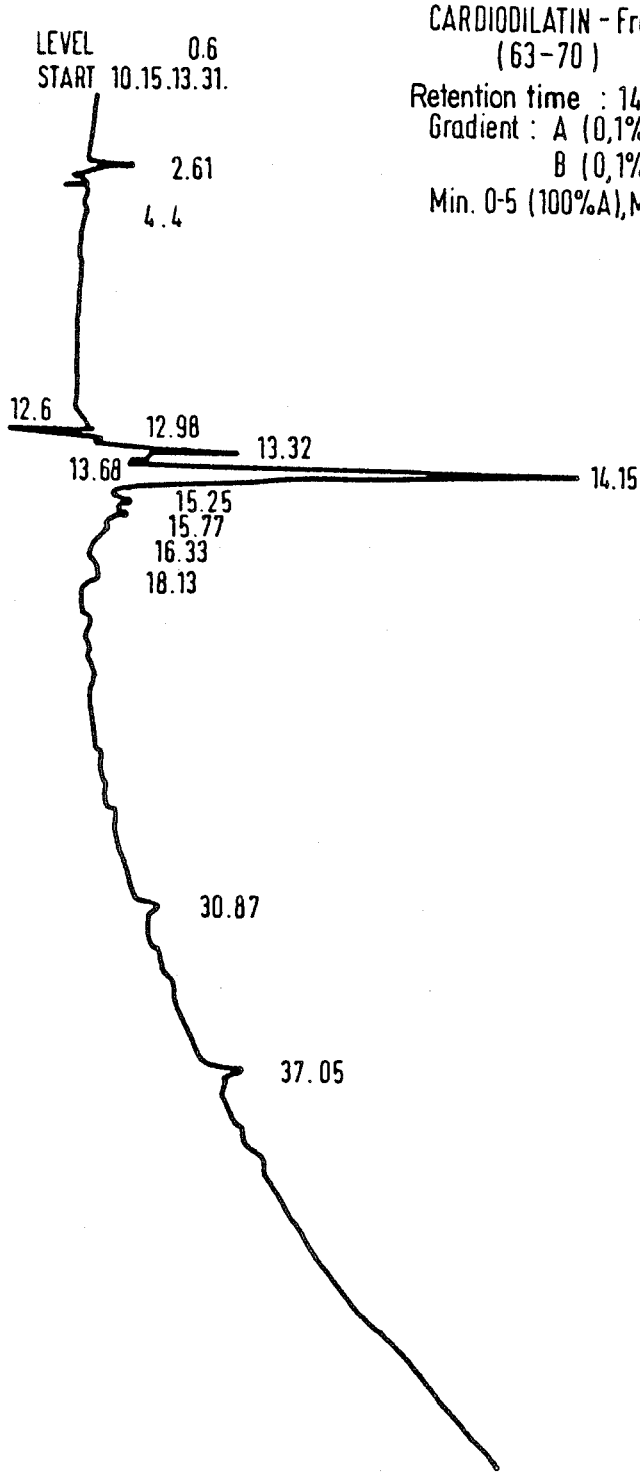
FIG. 6 shows a graphic illustration of the HPLC curve of cardiodilatin fragment (63–70).
Figure 7:
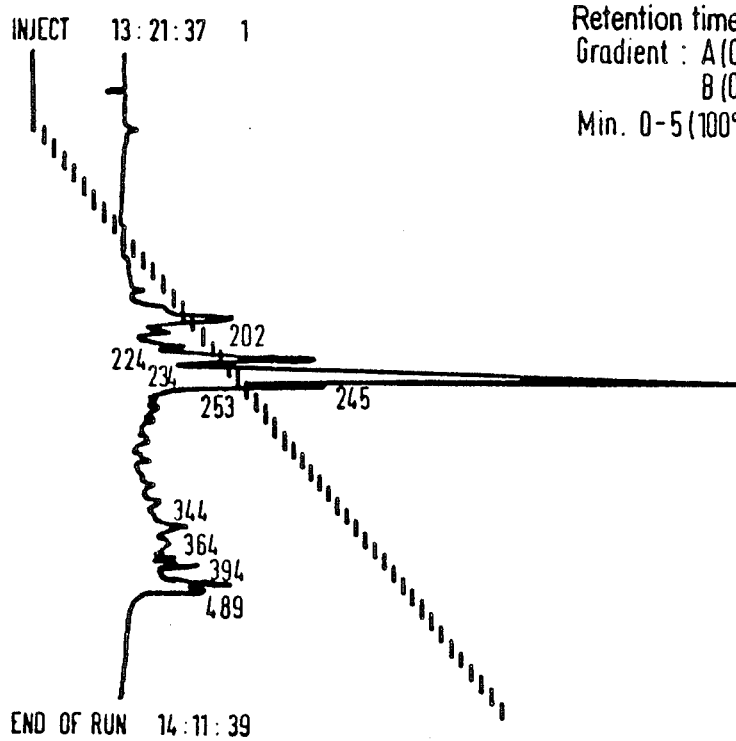
FIG. 7 shows a graphic illustration of the HPLC curve of cardiodilatin fragment (78–84).
Figure 8:
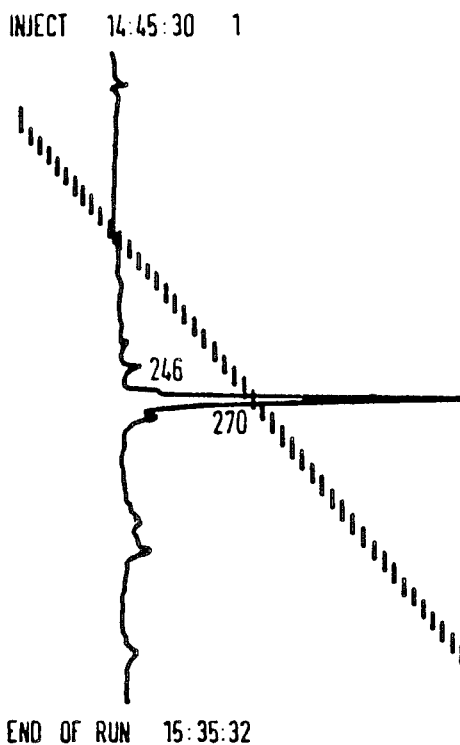
FIG. 8 shows a graphic illustration of the HPLC curve of cardiodilatin fragment (96–104).
Figure 9:
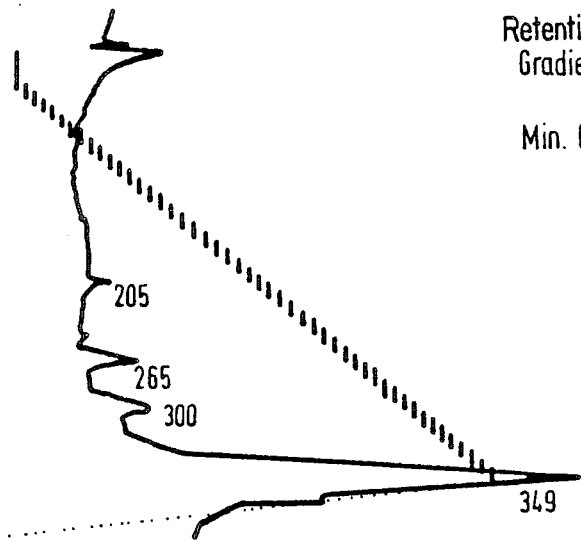
FIG. 9 shows a graphic illustration of the HPLC curve of cardiodilatin fragment (108–114), Tyr (Pos. 107).

In the case of N-terminal lengthening of the fragment 39 to 126 by one or more amino acids of the sequence 7 to 38 of the complete cardiodilatin in such a manner that a fragment always results which is identical in the sequence 7 to 126, one obtains fragments which also display the dilatory effectiveness of the complete cardiodilatin.

According to the invention, cardiodilatin is obtained in that one uses atrium extract as starting material and fractionates, according to usual biochemical purification methods, the material extractable with aqueous solvents with the use of a test in which the active fraction is determined by the relaxing action on smooth musculature. Preferably, the pure preparation of the peptide hormone cardiodilatin takes place from atrium extracts, e.g. of pig atria (V. Mutt, Arkiv Kemi 15, 69–74 (1959). Preferably, cardiodilatin is prepared in that one extracts boiled atrium material with dilute acid. As dilute acid, there are suitable, above all, the carboxylic acids but mineral acids can also be used. Preferably, one uses acetic acid, especially preferably in a concentration of 0.1 to 0.3M.

According to the invention, the further purification can so take place that one adsorbs the acid extract on alginic acid, again elutes the peptides with dilute mineral acid from the alginic acid, subjects the eluate to a salt precipitation, dissolves the precipitate thereby formed and again precipitates with ethanol. The ethanol precipitate is then dissolved and chromatographed over carboxymethylcellulose. A material so obtained is, as a rule, sufficiently pure for pharmaceutical or analytical purposes. The above-described precipitate obtained by salt precipitation can, alternatively, also be desalted directly and purified by gel chromatography, preferably on Sephadex G 25.

A fine purification is possible by means of high pressure liquid chromatography (HPLC) on a reverse phase silica gel (gradient elution: 0.1% trifluoroacetic acid in water against acetonitrile, 0 to 60%) and separation of the active fractions.

Expediently, the HPLC on a reverse phase silica gel is preceded by an HPLC on an ion exchanger column and/or the HPLC on reverse phase silica gel is repeated once or twice, preferably twice.

The N-terminal fragments, which are obtained either synthetically or by fission on the N-terminal methionine residue or arginine residue, bring about, after conjugation with a carrier protein, antibody formation in the case of administration to other animal types, such as rabbits or mice (Balb C), thus display hapten properties. These antibodies can be used as specific ligand in the affinity chromatography for the enrichment (isolation) and for the detection of the peptide hormone cardiodilatin. The affinity chromatography with an N-terminal fragment antibody as specific ligand thus represents a further suitable process for the enrichment (isolation) of the peptide hormone with which cardiodilatin can mostly already be obtained in sufficiently pure form. The affinity chromatography can also be employed with one of the above-mentioned chromatographic processes for the isolation of the peptide hormone or, however, one of the chromatographic methods can be followed by further purification according to one or more processes suitable therefor; suitable processes are e.g. electrophoresis, precipitation, adsorption chromatography, ion exchanger chromatography, affinity chromatography, isoelectric focussing or a combination of one or more identical or different ones of these steps.

The fragments present between two Met residues of the peptide chain can be prepared from the cardiodilatin in per se known manner by fission with suitable hydrolases but the fragments can also be prepared, such as e.g. the above-mentioned fragments with the amino sequence (1) and (2) or N-terminal fragments, by synthetic ways by per se known peptide syntheses, such as e.g. according to the method of Merrifield or synthesis with mixed anhydrides in solution.

As differentiating bioassay for the action of the peptide, there is used the relaxing effect in Arteria renalis (rabbit), Aorta abdominalis (rabbit, rat) and Arteria mesenterica inferior (rabbit) in an organ bath, whereby the blood vessel muscle strips contracted after adrenalin pretreatment show a distinct relaxation after the addition of cardiodilatin. This relaxation of the muscle strip from Arteria renalis is detectable after small doses of about 10 ng. to 100 ng./10 ml. of organ bath. In the case of strips of the aorta as test muscle, a detectable relaxation manifests itself at an about 10 times higher dosage, whereas on the Arteria mesenterica inferior of the rabbit, an activity was scarcely observed.

These biological actions show that the peptide hormone cardiodilatin and, as has been found, also its fragments, especially the C-terminal ones which stand after or between Met residues and can be obtained by partial cyanogen bromide fission, possess a great clinical (diagnostic) and therapeutic importance, namely, especially with regard to:

1. Differentiated vasodilation of certain beds of blood vessels,
2. diagnosis of hypertonia,
3. therapy of hypertonia,
4. possibility of diagnosing auricular dilations on the basis of the liberation of the hormone, and
5. use of this peptide hormone as substitution in the case of patients to whom artificial hearts have been implanted.
6. Furthermore, a synchronic regulation of the blood volume and of the blood electrolytes is conjectured on which the peptide has influence.
7. Skin diseases, especially with disturbance of the secretion of perspiration,
8. cardiovascular shock,
9. diseases of the kidney and adrenal cortex,
10. diseases of the digestive tract, especially of motility disturbances.

The subject of the invention are, therefore, also medicaments for use in the case of the above-stated diagnostic and therapy processes which contain the new peptide hormone cardiodilatin and/or active fragments thereof. The medicaments can be present in the usual forms of administration for oral or parenteral administration, such as e.g. as tablets, suppositories, dragrees, solutions etc., possibly together with usual, pharmacologically acceptable carrier and/or dilution agents. The amount of cardiodilatin preferably amounts to 10 to 1000 ng./dosage unit.

EXAMPLE 1

With the use of conventional electron-microscopic methods, those places were determined in the right atrium of pigs' hearts which display the highest density of myoendocrine cells (endocrine secretion grannular). These cells were mainly found on the thin-walled places of the auricle. Having regard to their size distribution (230 and 50 nm.) and their electron density, these pig granula are comparable with the human granula; the number of the granula amounts to about 0.02 to 0.04 granula/$\mu m^2$ of the cut surface.

This above-described tissue of the right atrium was removed from 20,000 pig hearts and extracted according to known processes (cf. V. Mutt, Arkiv Kemi 15, 69–74 (1959), S. I. Said and V. Mutt, Eur. J. Biochem. 28, 199–204 (1972), V. Mutt, Gut hormones, pp 21–27, S. R. Bloom/editor), Edinburgh-London-New York: Churchill Livingstone, 1978).

EXAMPLE 2

For this purpose, 40 kg. of pig atrium was boiled and extracted with 0.2M acetic acid. The filtrate was adsorbed on alginic acid, the alginic acid washed with ethanol and subsequently eluted with 0.2M hydrochloric acid. The eluate containing the peptides is then mixed with salt until the peptides precipitate out and the precipitate centrifuged off. The precipitate is again dissolved in phosphate buffer, pH 7, and again precipitated by the addition of ethanol. The precipitate was again dissolved in phosphate buffer, pH 6.4, and applied to a carboxymethylcellulose. The column had been previously equilibrated with a buffer containing 0.03M NaOH, 0.025M $H_3PO_4$, 0.5% thiodiglycol, pH 6.4. After elution with the same buffer, there took place a further elution with a buffer containing 0.03M NaOH, 0.025M $H_3PO_4$ and 0.2M NaCl, pH 6.4. The most active fractions were hereby eluted.

The fraction eluted with the sale-containing buffer is applied to an ion exchanger column (TSK carboxymethylcellulose of the Firm LKB) and eluted with 0.03M sodium phosphate buffer, pH 6.4, and a sodium chloride gradient of 0 to 0.5M. The active fraction is collected, desalted over a molecular sieve (Sephadex G 25 ®)) and subjected to preparative high pressure liquid chromatography (HPLC) with reversed phase, preferably with the use of an Organogen $C_{18}-5\mu$ ® column.

column: Waters $C_{18}-\mu$ Bondapak, $4\times250$ nm.

gradient elution: 0.1% trifluoroacetic acid in water against acetonitrile, 0 to 60% in 45 minutes.

The peptide cardiodilatin emerges at 45% acetonitrile from the HPLC column and displays a retention time of 24.1 minutes.

FIG. 1 shows a graphic illustration of this HPLC.

The active fraction obtained was thereafter again subjected twice to the same HPLC.

The isoelectric point I.P. was determined with 6 to 6.5.

The peptide showed, in the amino acid analysis, the following composition:

Asp/Asn 14, Thr 3, Ser 15, Glu/Gln 12, Pro 10, Gly 12, Ala 10, Val 7, Met 4, Ile 1, Leu 15, Tyr 2, Phe 3, Lys 4, His 2, Arg 10, Trp 2.

The amino acid sequence was determined, starting from the N-terminus, by automated Edman breakdown, as follows:

Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Glu-Gln-Asp-Glu-Glu-Val-Gly-Ala-Pro-Leu-Pro-Leu-Leu-Glu-Glu-Val-Pro-Pro-Trp-Thr-Gly-Glu-Val-Asn-Pro (according to the sequence analysis, the whole sequence included 126 amino acid residues)

On the basis of the amino acid composition, there is calculated a molecular weight of about 13000 Dalton.

For the various stages of the purification process, biological tests were carried out according to the following bioassay, whereby, with progressive degree of purification, an increase of the specific activity was shown. Carrying out of the bioassay:

Bioassays were carried out on smooth musculature in which was determined the relaxation in an organ bath due to the action of the fractions to be tested.

I claim:

1. Composition useful in treating a disease characterized by irregularities in tension or dilation of blood vessels, comprising an ionatropic effective amount of substantially pure peptide hormone cardiodilatin or a fragment thereof, said cardiodilatin characterized by having an isoelectric point of from 6 to 6.5, 126 amino acid residues, and an amino acid composition of Asp/Asn 14, Thr 3, Ser 15, Glu/Gln 12, Pro 10, Gly 12, Ala 10, Val 7, Met 4, Ile 1, Leu 15, Tyr 2, Phe 3, Lys 4, His 2, Arg 10, and Trp 2, and a pharmaceutically acceptable carrier.

2. Composition of claim 1, wherein said cardiodilatin has N-terminal amino acid sequence:
Asn-Pro-Val-Tyr-Gly-Ser-Val-Ser-Asn-Ala-Asp-Leu-Met-Asp-Phe-Lys-Asn-Leu-Leu-Asp-His-Leu-Glu-Asp-Lys-Met-Pro-Leu-Glu-Asp-Glu-Ala-Met-Pro-Pro-Gln-Val-Leu-Ser-Gly-Gln-Asp-Glu-Glu-Val-Gly-Ala-Pro-Leu-Pro-Leu-Leu-Glu-Glu-Val-Pro-Pro-Trp-Thr-Gly-Glu-Val-Asn-Pro 3. Composition of claim 1, wherein said composition comprises a cardiodilatin fragment with a sequence selected from the group consisting of:
Asp-Phe-Lys-Asn-Leu-Leu-Asp-His-Leu-Glu-Asp-Lys-Hse;
Pro-Leu-Glu-Asp-Glu-Ala-Hse; or
Asn-Pro-Val-Tyr-Gly-Ser-Val-Ser-Asn-Ala-Asp-Leu-Hse.

4. Composition of claim 1, wherein said composition comprises a cardiodilatin fragment with amino acid sequence selected from the group consisting of:
(a) A-Asp-Pro-X-Tyr-Y-Z-Val where X is Val or Met, Y is Gly or Val, Z is Ser or Ala, and A is H or Lys-Lys;
(b) Ser-Asn-Ala-Asp-Leu-Met-Asp-Phe-Lys-Asn-Leu-Leu;
(c) Glu-B-Lys-Met-Pro-Leu where B is Asp or Glu;
(d) Glu-Asp-Glu-C-D-Pro-Pro-Gln-E where C is Ala or Val, D is Met or Val, and E is Val or Glu;
(e) Leu-Ser-Glu-F-G-Glu-Glu where F is Pro or Gln and G is Asp or Asn;
(f) H-Pro-I-Gln-Arg-Asp-Gly-Gly where H is Asp or Ser and I is Ser or Ala;
(g) Gly-Arg-Gly-Pro-J-Asp-K where J is Trp or Phe and K is Pro or Ser;
(h) Asp-L-Ser-Asp-Arg-Ser-Ala, where L is Pro or Ser;
(i) Leu-Lys-Ser-Lys-Leu-Arg-Ala;
(j) M-Pro-Arg-Ser-Leu-Arg-Arg-Ser-Ser where M is Gly or Ala;
(k) N-Gly-Arg-Met-Asp-Arg-Ile where N is an optional Tyr;
(l) Tyr-Glu-Arg-Met-Asp-Arg-Ile-Gly;
(m) Ser-Gly-Leu-Gly-Cys-Asn-Ser-Phe-Arg-Tyr and dimeric sulphides thereof;
(n) Gly-Cys-Asn-Ser-Phe-Arg-Tyr and dimeric sulphides thereof;
(o) Ser-Glu-Gln-Asn-Glu-Glu-Val-Gly-Ala-Pro-Leu-Pro-Leu-Leu-Glu-Glu-Val-Pro-Pro-Trp-Thr-Gly-Glu-Val-Asp-Pro-Ser-Gln-Arg-Asp-Gly-Gly-Ala-Leu-Gly-Arg-Gly-Pro-Trp-Asp-Pro-Asp-Ser-Asp-Arg-Ser-Ala-Leu-Leu-Lys-Ser-Lys-Leu-Arg-Ala-Leu-Leu-Ala-Gly-Pro-Arg-Ser-Leu-Arg Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr, and
(p) Ser-Glu-Pro-Asn-Glu-Glu-Ala-Gly-Ala-Ala-Leu-Ser-Pro-Leu-Pro-Glu-Val-Pro-Pro-Trp-Thr-Gly-Glu-Val-Ser-Pro-Ala-Gln-Arg-Asp-Gly-Gly-Ala-Leu-Gly-Arg-Gly-Pro-Trp-Asp-Pro-Ser-Asp-Arg-Ser-Ala-Leu-Lys-Ser-Lys-Leu-Arg-Ala-Leu-Leu-Ala-Gly-Pro-Arg-Ser-Leu-Arg-Arg-Ser Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr, as well.

5. Method for obtaining substantially pure peptide hormone cardiodilatin, comprising extracting an atrium extract with an aqueous solvent in which said hormone is soluble, to obtain an extract of said hormone adsorbing said extract on an adsorbing agent to remove said hormone therefrom, eluting said removed hormone from said adsorbing agent, salt precipitating said hormone, dissolving precipitate, reprecipitating, and chromatographing to obtain said cardiodilatin.

6. Method of claim 5, wherein said aqueous solvent is a dilute acid.

7. Method of claim 5, wherein said adsorbing agent is algenic acid.

8. Method of claim 5, wherein said eluting comprises eluting with a mineral acid.

9. Method of claim 5, wherein said chromatographing comprises chromatographic in carboxymethy-cellulose.

10. Method of claim 6, wherein said acid is acetic acid.

11. Composition of claim 1, wherein said composition comprises from 10 to 1000 ng of cardiodilatin or fragment thereof per dosage unit.

12. Composition of claim 1, wherein said composition is in a form suitable for oral administration.

13. Composition of claim 1, wherein said composition is in a form suitable for parenteral administration.

14. Composition of claim 1, wherein said composition further comprises a dilution agent.

15. Composition of claim 9, wherein said composition is in the form of a tablet, a suppository, a dragee, or a solution.

* * * * *